United States Patent
Vangara et al.

(10) Patent No.: US 9,855,234 B2
(45) Date of Patent: Jan. 2, 2018

(54) DICLOFENAC SUBLINGUAL SPRAY

(71) Applicant: Insys Pharma, Inc., Chandler, AZ (US)

(72) Inventors: Kiran Kumar Vangara, Chandler, AZ (US); Daniela Bockenstedt, Chandler, AZ (US); Ningxin Yan, Chandler, AZ (US); Rajesh Pandya, Chandler, AZ (US); Venkat R. Goskonda, Phoenix, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 101 days.

(21) Appl. No.: 14/791,567

(22) Filed: Jul. 6, 2015

(65) Prior Publication Data

US 2016/0008306 A1    Jan. 14, 2016

Related U.S. Application Data

(60) Provisional application No. 62/022,049, filed on Jul. 8, 2014.

(51) Int. Cl.
| | | |
|---|---|---|
| *A61K 31/196* | (2006.01) | |
| *A61K 38/28* | (2006.01) | |
| *A61K 9/00* | (2006.01) | |
| *A61K 47/10* | (2017.01) | |
| *A61K 9/12* | (2006.01) | |

(52) U.S. Cl.
CPC ............ *A61K 31/196* (2013.01); *A61K 9/006* (2013.01); *A61K 47/10* (2013.01)

(58) Field of Classification Search
None
See application file for complete search history.

(56) References Cited

U.S. PATENT DOCUMENTS

| | | |
|---|---|---|
| 5,785,989 A | 7/1998 | Stanley et al. |
| 6,720,001 B2 | 4/2004 | Chen et al. |
| 6,923,988 B2 | 8/2005 | Patel et al. |
| 6,932,983 B1 | 8/2005 | Straub et al. |
| 7,759,394 B2 | 7/2010 | Reiner et al. |
| 2002/0142050 A1 | 10/2002 | Straub et al. |
| 2003/0138490 A1 | 7/2003 | Hu et al. |
| 2005/0266088 A1 | 12/2005 | Hinrichs et al. |
| 2008/0103092 A1* | 5/2008 | Pomytkin ............ A61K 9/0021 424/600 |
| 2009/0181080 A1* | 7/2009 | Kottayil ............... A61K 9/0014 424/456 |
| 2010/0086495 A1 | 4/2010 | Rubinstein |
| 2012/0003316 A1 | 1/2012 | Reddy et al. |

\* cited by examiner

*Primary Examiner* — Michael Barker
(74) *Attorney, Agent, or Firm* — Wood, Phillips, Katz, Clark & Mortimer

(57) ABSTRACT

The present invention is directed to diclofenac sublingual spray formulations. The present invention is also directed to methods for treating pain and inflammation by administering the formulations of the present invention to patients in need thereof.

18 Claims, No Drawings

DICLOFENAC SUBLINGUAL SPRAY

FIELD OF THE INVENTION

The present invention is generally directed to diclofenac sublingual spray formulations, and methods of their use.

BACKGROUND

Diclofenac, [(2,6-dichloro-anilino)-2-phenyl]-2-acetic acid, is a nonsteroidal anti-inflammatory drug (NSAID) with the following structure:

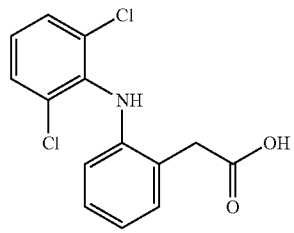 [SMILES: O=C(O)Cc1ccccc1Nc1c(Cl)cccc1Cl]

Diclofenac also has analgesic and antipyretic properties. Diclofenac works by blocking cyclooxygenase. The blocked cyclooxygenase fails to trigger production of prostaglandins, which are responsible for creating pain, swelling and inflammation in response to injury and certain conditions.

Diclofenac is commercially available as a tablet from Novartis (e.g., Cataflam®; Cataflam is a registered trademark of Novartis Corporation). The Orange Book (The Food and Drug Administration's publication listing drug products approved under section 505 of the Federal Food, Drug, and Cosmetic Act) indicates that diclofenac has also been formulated as a capsule, patch, and gel. Diclofenac has also been administered via injection and rectal suppositories.

Diclofenac has been administered for the treatment of many conditions and disorders including migraines, rheumatoid arthritis, osteoarthritis, actinic keratosis, ankylosing spondylitis, bursitis, tendonitis, soft tissue disorders such as sprains and strains, renal colic, acute gout, dysmenorrhea, and pain following surgery.

U.S. Pat. No. 7,759,394 is directed to methods of treating migraines associated with phonophobia and photophobia that involve administration and ingestion of a liquid 50 milligrams diclofenac formulation in combination with an alkali metal carbonate or bicarbonate. One problem with ingestion of such a formulation is that diclofenac is subject to the hepatic first pass metabolic process that decreases bioavailability. Another disadvantage of such a formulation is that some patients have difficulty swallowing (dysphagia). In addition, drugs that are ingested (e.g. tablets, capsules, solutions) must be absorbed into the blood stream through the stomach or intestine which causes a delay in action.

Patches and gels containing diclofenac may lead to dryness, redness, itching, swelling, irritation, or numbness at the application site(s). Patches and gels are also limited to the treatment of pain or swelling in proximity to the transdermal application site.

Diclofenac has been proven to provide relief from many conditions. While some diclofenac formulations are available to patients in need of diclofenac treatment, there is still a need for new diclofenac formulations with quicker on-set, higher bioavailability, and improved storage stability.

SUMMARY OF THE INVENTION

In one aspect, the present invention is directed to sublingual spray formulations comprising from about 5 to about 40% diclofenac, or a salt thereof, from about 1 to about 50% polar solvent, and from about 5 to about 30% co-solvent.

In another aspect, the present invention is directed to sublingual spray formulations comprising from about 5 to about 40% diclofenac, or a salt thereof, from about 1 to about 50% polar solvent selected from the group consisting of water, ethanol and a combination thereof, and from about 5 to about 30% co-solvent.

In another aspect, the present invention is directed to sublingual spray formulations comprising from about 5 to about 40% diclofenac, or a salt thereof, from about 1 to about 50% polar solvent, and from about 5 to about 30% co-solvent selected from the group consisting of propylene glycol, a low molecular weight polyethylene glycol, and a combination thereof.

In another aspect, the present invention is directed to sublingual spray formulations comprising from about 5 to about 40% diclofenac, or a salt thereof, from about 1 to about 50% polar solvent, from about 5 to about 30% co-solvent, and an excipient selected from the group consisting of one or more permeation enhancers, flavoring agents, sweeteners, sweetness enhancers, taste-masking agents, and a combination thereof.

In another aspect, the present invention is directed to sublingual spray formulations comprising from about 5 to about 40% diclofenac, or a salt thereof, from about 1 to about 50% polar solvent, from about 5 to about 30% co-solvent, and an excipient selected from the group consisting of one or more permeation enhancers, flavoring agents, sweeteners, sweetness enhancers, taste-masking agents, and a combination thereof, wherein the one or more flavoring agents is peppermint oil, the one or more sweeteners is sucralose, the one or more sweetness enhancers is ammonium salt of glycyrrhizic acid, and the one or more taste-masking agents are sodium chloride and polyethoxylated castor oil.

In another aspect, the present invention is directed to sublingual spray formulations comprising from about 5 to about 40% diclofenac, or a salt thereof, from about 1 to about 50% polar solvent, and from about 5 to about 30% co-solvent, wherein the sublingual spray formulation is capable of producing a droplet size distribution wherein greater than 98% of the composition particles are greater than 10 microns in diameter during administration.

In another aspect, the present invention is directed to sublingual spray formulations comprising from about 5 to about 40% diclofenac, or a salt thereof, from about 1 to about 50% polar solvent, and from about 5 to about 30% co-solvent, wherein the sublingual spray formulation is capable of producing a droplet size distribution wherein the mean Dv(10) is from about 10 to about 40 microns during administration; the mean DV(50) is from about 50 to about 180 microns during administration; and the mean DV(90) is from about 300 to about 700 microns during administration.

In another aspect, the present invention is directed to sublingual spray formulations comprising from about 5 to about 40% diclofenac, or a salt thereof, from about 1 to about 50% polar solvent, and from about 5 to about 30% co-solvent, wherein the sublingual spray formulation is capable of producing a spray span ((Dv90−Dv10)/Dv50) of from about 1.5 to about 8.

In another aspect, the present invention is directed to sublingual spray formulations comprising from about 5 to about 40% diclofenac, or a salt thereof, from about 1 to about 50% polar solvent, and from about 5 to about 30% co-solvent, wherein the sublingual spray formulation is capable of producing a spray that has an ovality ratio of from about 1.1 to about 2; a spray plume width that is from about 10 to about 50 millimeters during administration; and a spray plume angle that is from about 20 to about 50 degrees during administration.

In another aspect, the present invention is directed to treating pain, preferably selected from the group consisting of acute migraine, osteoarthritis, rheumatoid arthritis, and inflammation associated pain by administration of the diclofenac formulations of the present invention to patients in need of treatment for pain or inflammation.

In another aspect, the present invention is directed to a method of preventing crystal growth in diclofenac spray formulations comprising adding at least 5% propylene glycol, at least 1% polyethylene glycol, and less than 50% water.

DETAILED DESCRIPTION

Applicant developed new diclofenac formulations that are easy to administer, have quick on-set and high bioavailability. The formulations unexpectedly showed excellent stability at low storage temperatures and at ambient temperature over long periods of time.

In an embodiment, the present invention is directed to sublingual spray formulations comprising from about 5 to about 40% diclofenac, or a salt thereof, from about 1 to about 50% polar solvent, and from about 5 to about 30% co-solvent.

The diclofenac salt may be any pharmaceutically suitable salt. In a preferred embodiment, the salt is potassium or sodium salt. In a more preferred embodiment, the salt is the potassium salt.

In another embodiment, the formulations of the present invention contain from about 15 to about 35% diclofenac, or salt thereof. In a preferred embodiment, the formulations of the present invention contain from about 20 to about 30% diclofenac, or salt thereof. In a more preferred embodiment, the formulations of the present invention contain from about 24 to about 26% diclofenac, or salt thereof.

In an embodiment, the formulations of the present invention contain from about 1 to about 50% polar solvent. In a preferred embodiment, the formulations of the present invention contain from about 10 to about 35% polar solvent. In a more preferred embodiment, the formulations of the present invention contain from about 15 to about 30% polar solvent.

In another embodiment, the polar solvent is selected from the group consisting of water, ethanol and a combination thereof.

In an embodiment, the formulations of the present invention contain from about 5 to about 35% ethanol. In a preferred embodiment, the formulations of the present invention contain from about 10 to about 30% ethanol. In a more preferred embodiment, the formulations of the present invention contain from about 15 to about 25% ethanol.

In an embodiment, the formulations of the present invention contain from about 15 to about 45% water. In a preferred embodiment, the formulations of the present invention contain from about 20 to about 40% water. In a more preferred embodiment, the formulations of the present invention contain from about 25 to about 35% water.

In another embodiment, the formulations of the present invention contain from about 5 to about 30% co-solvent.

In another embodiment, the co-solvent is selected from the group consisting of propylene glycol, a low molecular weight polyethylene glycol, and a combination thereof. As used herein, "co-solvent" does not include water or ethanol.

In another embodiment, the formulations of the present invention contain from about 0.1 to about 40% propylene glycol. In a preferred embodiment, the formulations of the present invention contain from about 5 to about 35% propylene glycol. In a more preferred embodiment, the formulations of the present invention contain from about 5 to about 25% propylene glycol. In a yet more preferred embodiment the formulations of the present invention contain from about 10 to about 20% propylene glycol.

In yet another embodiment, the formulations of the present invention contain from about 0.1 to about 40% of a low molecular weight polyethylene glycol. In a preferred embodiment, the formulations of the present invention contain from about 1 to about 30% of a low molecular weight polyethylene glycol. In a more preferred embodiment, the formulations of the present invention contain from about 1 to about 20% of a low molecular weight polyethylene glycol. In a yet more preferred embodiment, the formulations of the present invention contain from about 5 to about 15% of a low molecular weight polyethylene glycol.

Low molecular weight polyethylene glycols have an average molecular weight of between 200 and 10,000. In a more preferred embodiment, the polyethylene glycol is polyethylene glycol 400 ("PEG400").

In a further embodiment, the formulations of the present invention contain an excipient selected from the group consisting of one or more permeation enhancers, flavoring agents, sweeteners, sweetener enhancers, taste-masking agents, and a combination thereof.

In another embodiment, the permeation enhancer is oleic acid, polysorbate 80, L-menthol, butylated hydroxyanisole, ethylenediaminetetraacetic acid (EDTA), sodium edetate, cetylpyridinium chloride, sodium lauryl sulfate, citric acid, sodium desoxycholate, sodium deoxyglycolate, glyceryl oleate, L-lysine, or a combination thereof.

In preferred embodiments, the amount of permeation enhancer is from about 0.001% to about 5.0%. In a more preferred embodiment, the formulations contain from about 0.01% to about 1.0% permeation enhancer.

In preferred embodiment, the permeation enhancer is L-menthol. If the permeation enhancer is L-menthol, the preferred amount of L-menthol is from about 0.001% to about 5.0%. In a more preferred embodiment, the formulations contain from about 0.01% to about 1.0% L-menthol.

In another preferred embodiment, the flavoring agent is peppermint oil, spearmint oil, citrus oil, cinnamon oil, orange oil, anise oil, strawberry flavor, cherry flavor, raspberry flavor, anise flavor, mint flavor, cinnamon-mint flavor, peppermint-citrus flavor, fruit punch flavor, bitterness masking flavor, bitterness blocking flavor, or a combination thereof.

In a preferred embodiment, the formulations contain from about 0.001% to about 1% of the flavoring agent. In a more preferred embodiment, the formulations contain from about 0.005% to about 0.5% of the flavoring agent.

In yet another embodiment, the sweetener is sucrose, sucralose, aspartame, saccharin, dextrose, mannitol, glycerin, xylitol, neotame, acesulfame potassium, or a combination thereof.

In an embodiment, the formulations contain from about 0.001% to about 2% of the sweetener. In a more preferred embodiment, the formulations contain from about 0.02% to about 1.0% of the sweetener.

In another embodiment, the formulations contain a sweetness enhancer. The preferred sweetness enhancer is one selected from Magnasweet®'s product line (available from and a registered trademark of Mafco Worldwide Corporation). The Magnasweet® products use the ammonium salt forms of crude and refined glycyrrhizic acid. Glycyrrhizic acid is also available as a pure derivative in the sodium and potassium salt forms. Preferred sweetener enhancers are Magnasweet® 100, Magnasweet® 110, Magnasweet® 100F, Magnasweet® 200, Magnasweet® 300 or a combination thereof.

In an embodiment, the formulations contain from about 0.001% to about 2% of the sweetness enhancer. In a more preferred embodiment, the formulations contain from about 0.05% to about 1% of the sweetness enhancer.

In a preferred embodiment, the formulations contain a taste-masking agent. In a more preferred embodiment, the taste-masking agent is selected from the group consisting of sodium chloride, polyethoxylated castor oil, and a combination thereof. Kolliphor® RH 40 can be used as the source of polyethoxylated castor oil (Kolliphor® is available from and a registered trademark of BASF Corporation).

In an embodiment, the formulations contain from about 0.001% to about 5% of the taste-masking agent. In a more preferred embodiment, the formulations contain from about 0.05% to about 3% of the taste-masking agent.

In another embodiment, the present invention is directed to sublingual spray formulations comprising from about 15 to about 35% diclofenac, or a salt thereof, from about 15 to about 45% water, from about 5 to about 35% ethanol, and from about 6 to about 40% of a co-solvent. In a preferred embodiment, these formulations contain a combination of from about 5 to about 35% propylene glycol and from about 1 to about 30% polyethylene glycol 400 as the co-solvent.

In yet another preferred embodiment, the formulations contain from about 20 to about 30% diclofenac, or a salt thereof, from about 20 to about 40% water, from about 10 to about 30% ethanol, from about 5 to about 25% of propylene glycol, and from about 1 to about 20% polyethylene glycol 400. In a preferred embodiment, these formulations contain from about 25 to about 35% water, from about 15 to about 25% ethanol, from about 10 to about 20% of propylene glycol, and from about 5 to about 15% polyethylene glycol 400.

In an embodiment, the invention is directed to methods for treating pain comprising administering the formulations of the present invention to a patient in need of pain treatment. In a preferred embodiment, the pain is due to migraines, acute migraines, arthritis such as osteoarthritis and rheumatoid arthritis, and pain associated with inflammation.

In an embodiment, the invention is directed to methods for treating inflammation comprising administering the formulations of the present invention to a patient in need of inflammation treatment. In a preferred embodiment, the inflammation is due to an autoimmune disorder such as arthritis. In another preferred embodiment, the pain is due to an injury or a surgery.

In a preferred embodiment, the formulations of the present invention are administered to a patient transmucosally. In a more preferred embodiment, the formulations of the present invention are administered sublingually. In a most preferred embodiment, the formulations are administered sublingually with a spray pump. In a preferred embodiment, no propellant is necessary to administer the formulation.

When formulations of the present invention are administered sublingually with a spray pump, from about 50 to about 200 μL of the formulation is administered to the patient in each dose.

As used herein, "sublingual" means "under the tongue" and refers to administration of a substance via the mouth in such a way that the substance is rapidly absorbed via the blood vessels under the tongue. As discussed above, sublingual formulations are desirable because they bypass the hepatic first pass metabolic process and therefore provide better bioavailability, rapid onset of action, and higher patient compliance. In terms of permeability, the sublingual area of oral cavity is even more permeable than buccal area.

In a further embodiment, the formulations of the present invention are capable of producing a droplet size distribution wherein greater than 98% of the composition particles are greater than 10 microns in diameter during administration.

In another embodiment, the formulations of the present invention are capable of producing a droplet size distribution wherein the mean Dv(10) is from about 10 to about 40 microns during administration.

In yet another embodiment, the formulations of the present invention are capable of producing a droplet size distribution wherein the mean Dv(50) is from about 50 to about 180 microns during administration.

In a further embodiment, the formulations of the present invention are capable of producing a droplet size distribution wherein the mean Dv(90) is from about 300 to about 700 microns during administration.

In another embodiment, the formulations of the present invention are capable of producing a spray span ((Dv90−Dv10)/Dv50) of from about 1.5 to about 8.

In an embodiment, the formulations of the present invention are capable of producing a spray plume that has an ovality ratio of from about 1.1 to about 2.

In a further embodiment, the formulations of the present invention are capable of producing a spray plume width that is from about 10 to about 50 millimeters during administration.

In another embodiment, the formulations of the present invention are capable of producing a spray plume angle that is from about 20 to about 50 degrees during administration.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

The percentages of the components of the formulations are expressed in percent weight per weight of the formulation.

As used herein the term "effective amount" refers to the amount necessary to treat a patient in need thereof.

As used herein the term "pharmaceutically acceptable" refers to ingredients that are not biologically or otherwise undesirable in an oral dosage form.

As used herein the phrase "propellant free" refers to a formulation that is not administered using compressed gas.

As used herein the term "patient" refers to a single patient and not a patient population.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

All claims, aspects and embodiments of the invention, and specific examples thereof, are intended to encompass equivalents thereof.

EXAMPLES

Example 1

A diclofenac formulation was prepared as follows using the components and amounts listed for Formulation #3 in Table 1 below. All of the solvents were purged with nitrogen before use. The aqueous phase was prepared by dissolving sucralose and sodium chloride in water. The alcohol phase was prepared by dissolving L-menthol in ethanol. Then the aqueous and alcohol phases were mixed together. To this solution propylene glycol and polyethylene glycol 400 were added and mixed thoroughly. A diclofenac salt was added to the excipient solution and mixed until dissolved. Then the flavoring agent, sweetness enhancer and taste masking agents were added and mixed until a homogenous solution was formed.

Diclofenac potassium was used as the source of the diclofenac salt. Peppermint oil was used as the source of flavoring agent. Magnasweet® 110 was used as the source of sweetness enhancer. Kolliphor® RH 40 glyceryl polyethylene glycol oxystearate and fatty acid glyceryl polyglyceryl esters and sodium chloride were used as the sources of the taste masking agents.

Formulations #1, #2, and #4 were prepared in a similar manner.

TABLE 1

Diclofenac Formulations

| | Formulation | | | |
|---|---|---|---|---|
| | #1 | #2 | #3 | #4 |
| Diclofenac salt | 24 | 24 | 23.3 | 23.3 |
| Polyethylene Glycol 400 | 10 | 10 | 10 | 10 |
| Propylene Glycol | 15 | 15 | 15 | 15 |
| Ethanol | 25.5 | 31 | 23.4 | 23.9 |
| Water | 25.5 | 20 | 23.5 | 24 |
| Sucralose | | | 2 | 2 |
| Flavoring agent | | | 0.35 | 0.35 |
| Taste masking agent-Sodium Chloride | | | 1.5 | 1.5 |
| Taste masking agent-polyethoxylated castor oil | | | 0.5 | |
| L-Menthol | | | 0.05 | |
| Sweetness enhancer | | | 0.4 | |

Example 2

The formulations listed in Table 1 were subjected to stability at 40° C.±2° C./75%±5% relative humidity and 25° C.±2° C./60%±5% relative humidity. The stability of the formulations were analyzed at specified time points by evaluating their potency (assay value) and impurity levels. Assay and impurities were detected using high-performance liquid chromatography with an ultraviolet detector. The assay was performed at 254 nm and indicated as a % of initial concentration. For all impurities, analysis was performed at 254 nm and expressed as a % area. Amounts of particular impurities are listed in Table 2 to 9 as a percentage of area of each formulation along with amount of total impurities. Relative retention time ("RRT") is given for each impurity. "ND" indicates that the impurity was not detected.

TABLE 2

Stability Data for Diclofenac Sublingual Spray Formulation #1 stored at 40° C. ± 2° C./75% ± 5% Relative Humidity

| | | Formulation #1 | | |
|---|---|---|---|---|
| 40° C. | RRT | 0 month | 3 month | 6 month |
| Assay (% of initial concentration) | | 100.00 | 98.48 | 97.56 |
| % Impurity A | 0.39 | ND | 0.01 | 0.01 |
| % Unknown Impurity | 0.44 | 0.02 | 0.02 | 0.01 |
| | 0.69 | ND | ND | ND |
| | 0.71 | ND | 0.03 | 0.02 |
| | 0.78 | ND | 0.08 | 0.14 |
| | 1.08 | ND | 0.01 | 0.02 |
| Total % (% Area) | | 0.02 | 0.16 | 0.21 |

TABLE 3

Stability Data for Diclofenac Sublingual Spray Formulation #2 stored at 40° C. ± 2° C./75% ± 5% Relative Humidity

| | | Formulation #2 | | |
|---|---|---|---|---|
| 40° C. | RRT | 0 month | 3 month | 6 month |
| Assay (% of initial concentration) | | 100.00 | 97.98 | 97.92 |
| % Impurity A | 0.39 | ND | 0.01 | 0.01 |
| % Unknown Impurity | 0.44 | 0.02 | 0.02 | 0.01 |
| | 0.71 | ND | 0.03 | 0.03 |
| | 0.78 | ND | 0.07 | 0.14 |
| | 1.08 | ND | ND | 0.01 |
| Total % (% Area) | | 0.02 | 0.13 | 0.23 |

TABLE 4

Stability Data for Diclofenac Sublingual Spray Formulation #3 stored at 40° C. ± 2° C./75% ± 5% Relative Humidity

| | | Formulation #3 | | | |
|---|---|---|---|---|---|
| 40° C. | RRT | 0 month | 1 month | 3 month | 6 month |
| Assay (% of initial concentration) | | 100.00 | 99.74 | 99.08 | 101.27 |
| % Impurity A | 0.39 | ND | 0.02 | 0.05 | 0.05 |
| % Unknown Impurity | 0.44 | 0.02 | 0.02 | 0.01 | 0.01 |
| | 0.69 | ND | ND | 0.02 | 0.06 |
| | 0.71 | ND | ND | 0.03 | 0.05 |
| | 0.81 | ND | ND | 0.03 | 0.07 |
| | 1.07 | ND | ND | 0.05 | 0.10 |
| Total % (% Area) | | 0.02 | 0.04 | 0.20 | 0.34 |

TABLE 5

Stability Data for Diclofenac Sublingual Spray Formulation #4 stored at 40° C. ± 2° C./75% ± 5% Relative Humidity

| | | Formulation #4 | | | |
|---|---|---|---|---|---|
| 40° C. | RRT | 0 month | 1 month | 3 month | 6 month |
| Assay (% of initial concentration) | | 100.00 | 99.12 | 97.95 | 101.72 |
| % Impurity A | 0.39 | ND | 0.01 | 0.02 | 0.01 |
| % Unknown Impurity | 0.45 | 0.02 | 0.01 | 0.01 | 0.01 |
| | 0.70 | ND | ND | 0.03 | 0.03 |

TABLE 5-continued

Stability Data for Diclofenac Sublingual Spray Formulation #4 stored at 40° C. ± 2° C./75% ± 5% Relative Humidity

| 40° C. | RRT | Formulation #4 | | | |
|---|---|---|---|---|---|
| | | 0 month | 1 month | 3 month | 6 month |
| | 0.71 | ND | ND | 0.05 | 0.10 |
| | 0.81 | ND | ND | 0.07 | 0.12 |
| | 1.07 | ND | ND | 0.07 | 0.14 |
| Total % (% Area) | | 0.02 | 0.03 | 0.24 | 0.41 |

TABLE 6

Stability Data for Diclofenac Sublingual Spray Formulation #1 stored at 25° C. ± 2° C./60% ± 5% Relative Humidity

| 25° C. | RRT | Formulation #1 | | | | |
|---|---|---|---|---|---|---|
| | | 0 month | 3 month | 6 month | 9 month | 12 month |
| Assay (% of initial concentration) | | 100.00 | 99.35 | 97.90 | 97.70 | 98.15 |
| % Impurity A | 0.39 | ND | 0.00 | 0.01 | 0.01 | 0.01 |
| % Unknown Impurity | 0.44 | 0.02 | 0.02 | 0.01 | 0.02 | 0.02 |
| | 0.78 | ND | ND | 0.01 | 0.02 | 0.04 |
| Total % (% Area) | | 0.02 | 0.02 | 0.03 | 0.04 | 0.07 |

TABLE 7

Stability Data for Diclofenac Sublingual Spray Formulation #2 stored at 25° C. ± 2° C./60% ± 5% Relative Humidity

| 25° C. | RRT | Formulation #2 | | | | |
|---|---|---|---|---|---|---|
| | | 0 month | 3 month | 6 month | 9 month | 12 month |
| Assay (% of initial concentration) | | 100.00 | 98.37 | 100.25 | 98.08 | 97.05 |
| % Impurity A | 0.39 | ND | 0.01 | 0.01 | 0.01 | 0.01 |
| % Unknown Impurity | 0.44 | 0.02 | 0.02 | 0.02 | 0.02 | 0.02 |
| | 0.70 | ND | ND | ND | ND | 0.02 |
| | 0.78 | ND | ND | 0.01 | 0.02 | 0.03 |
| Total % (% Area) | | 0.02 | 0.03 | 0.04 | 0.05 | 0.08 |

TABLE 8

Stability Data for Diclofenac Sublingual Spray Formulation #3 stored at 25° C. ±2° C./60 % ± 5% Relative Humidity

| 25° C. | RRT | Formulation #3 | | | |
|---|---|---|---|---|---|
| | | 0 month | 1 month | 3 month | 6 month |
| Assay (% of initial concentration) | | 100.00 | 99.87 | 99.24 | 101.27 |
| % Impurity A | 0.39 | ND | ND | 0.01 | 0.02 |
| % Unknown Impurity | 0.45 | 0.02 | 0.02 | 0.02 | 0.02 |
| | 0.70 | ND | ND | ND | 0.01 |
| Total % (% Area) | | 0.02 | 0.02 | 0.03 | 0.05 |

TABLE 9

Stability Data for Diclofenac Sublingual Spray Formulation #4 stored at 25° C. ± 2° C./60% ± 5% Relative Humidity

| 25° C. | RRT | Formulation #4 | | | |
|---|---|---|---|---|---|
| | | 0 month | 1 month | 3 month | 6 month |
| Assay (% of initial concentration) | | 100.00 | 99.21 | 98.51 | 101.72 |
| % Impurity A | 0.39 | ND | ND | 0.00 | 0.01 |
| % Unknown Impurity | 0.45 | 0.02 | 0.01 | 0.01 | 0.01 |
| | 0.70 | ND | ND | ND | 0.01 |
| | 0.71 | ND | ND | ND | 0.01 |
| | 0.81 | ND | ND | ND | 0.01 |
| | 1.07 | ND | ND | ND | 0.02 |
| Total % (% Area) | | 0.02 | 0.01 | 0.02 | 0.06 |

Formulations #1, #2, #3, and #4 had very low amounts of impurities at both 40° C.±2° C./75%±5% relative humidity and 25° C.±2° C./60%±5% relative humidity. The superior stability characteristics of the formulations of the present invention will allow the formulations to be effective when used by patients.

Example 3

Additional diclofenac salt formulations were prepared according to the procedures of Example 1 and tested for physical stability at 5° C.±3° C., 15° C.±2° C., and 25° C.±2° C. After storage, the formulations were examined for crystal formation. The results of this study can be seen below in Table 10.

TABLE 10

Diclofenac Formulation Physical Stability

| Diclofenac salt | % weight | | | | Physical Stability | | |
|---|---|---|---|---|---|---|---|
| | Water | Dehydrated Alcohol | Propylene Glycol | PEG400 | 5 ± 3° C. | 15 ± 2° C. | 25 ± 2° C. |
| 25 | 29 | 36 | 0 | 10 | Crystals | Clear | Clear |
| 25 | 27.5 | 27.5 | 0 | 20 | Clear | Clear | Clear |
| 25 | 20 | 35 | 0 | 20 | Clear | Clear | Clear |
| 25 | 25 | 35 | 5 | 10 | Crystals | Clear | Clear |
| 25 | 27.5 | 27.5 | 10 | 10 | Crystals | Clear | Clear |
| 25 | 25 | 30 | 10 | 10 | Crystals | Clear | Clear |
| 25 | 20 | 35 | 10 | 10 | Clear | Clear | Clear |
| 25 | 25 | 30 | 15 | 5 | Crystals | Clear | Clear |
| 25 | 20 | 35 | 15 | 5 | Crystals | Clear | Clear |
| 24 | 35 | 16 | 15 | 10 | Crystals | Clear | Clear |
| 24 | 30 | 21 | 15 | 10 | Crystals | Clear | Clear |
| 25 | 25 | 25 | 15 | 10 | Clear | Clear | Clear |
| 25 | 20 | 30 | 15 | 10 | Clear | Clear | Clear |
| 25 | 22.5 | 22.5 | 15 | 15 | Clear | Clear | Clear |
| 25 | 27.5 | 27.5 | 20 | 0 | Crystals | Clear | Clear |
| 25 | 20 | 35 | 20 | 0 | Crystals | Clear | Clear |
| 25 | 25 | 25 | 20 | 5 | Crystals | Clear | Clear |
| 25 | 22.5 | 22.5 | 20 | 10 | Clear | Clear | Clear |
| 25 | 20 | 25 | 20 | 10 | Clear | Clear | Clear |
| 25 | 20 | 20 | 35 | 0 | Clear | Clear | Clear |

Hydro-alcoholic sublingual spray formulations of diclofenac are prone to development of crystals. Crystal formation is especially problematic at higher concentrations and/or lower temperatures (i.e. 2 to 8° C.). Based on the results from the physical stability test (see, Table 10), it was found that crystal growth can be prevented by addition of at least 5% propylene glycol and/or at least 5% PEG400 and restricting water to less than 50%.

Example 4

In order to determine the spray profile of Formulation #3, it was subjected to standardized droplet testing. A challenge of creating a diclofenac sublingual spray formulation is that it must be capable of producing spray droplets that are over 10 microns in diameter. Spray droplets of 10 microns or smaller could be inhaled into the lungs.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation.

Spray pattern, specifically Dmin, Dmax, and ovality ratio were tested at two distances, 3 cm and 6 cm. Dmin refers to the shortest diameter of the spray pattern in mm, Dmax refers to the widest diameter of the spray pattern in mm, and ovality ratio refers to the ratio of Dmax to Dmin. The spay pattern is measured after impact onto an appropriate target upon activation of a spray pump. The ovality ratio is useful as it provides information regarding the shape and density of the spray pump plume.

The results of these tests can be seen below in Tables 11 to 16.

TABLE 11

Droplet size distribution of Diclofenac Sublingual Spray Formulation at 3 cm

| DSD 3 cm 25° C. | $DV_{10}$ | $DV_{50}$ | $DV_{90}$ | Span |
|---|---|---|---|---|
| Min | 22.57 μm | 83.41 μm | 546.5 μm | 2.228 |
| Max | 26.36 μm | 322.1 μm | 744.1 μm | 6.430 |
| Mean | 24.0 μm | 164.2 μm | 624.7 μm | 4.977 |

TABLE 12

Droplet size distribution of Diclofenac Sublingual Spray Formulation at 6 cm

| DSD 6 cm 25° C. | $DV_{10}$ | $DV_{50}$ | $DV_{90}$ | Span |
|---|---|---|---|---|
| Min | 24.23 μm | 62.17 μm | 415.8 μm | 5.566 |
| Max | 25.92 μm | 70.89 μm | 547 μm | 7.327 |
| Mean | 25.9 μm | 67.7 μm | 478.7 μm | 6.706 |

TABLE 13

Spray pattern of Diclofenac Sublingual Spray Formulation at 3 cm

| SP 3 cm 25° C. | Dmin | Dmax | Ovality ratio |
|---|---|---|---|
| Min | 15.6 mm | 19.3 mm | 1.239 |
| Max | 17.5 mm | 22.5 mm | 1.323 |
| Mean | 16.7 mm | 21.4 mm | 1.282 |

TABLE 14

Spray pattern of Diclofenac Sublingual Spray Formulation at 6 cm

| SP 6 cm 25° C. | Dmin | Dmax | Ovality ratio |
|---|---|---|---|
| Min | 20.5 mm | 29.9 mm | 1.294 |
| Max | 23.1 mm | 32.6 mm | 1.587 |
| Mean | 21.7 mm | 31.3 mm | 1.447 |

TABLE 15

Plume geometry of Diclofenac Sublingual Spray Formulation at 3 cm

| Plume Geometry 3 cm 25° C. | Angle | Width |
|---|---|---|
| Min | 30.9 deg | 16.7 mm |
| Max | 47.6 deg | 26.6 mm |
| Mean | 41.6 deg | 23.0 mm |

TABLE 16

Plume geometry of Diclofenac Sublingual Spray Formulation at 6 cm

| Plume Geometry 6 cm 25° C. | Angle | Width |
|---|---|---|
| Min | 33.2 deg | 36.2 mm |
| Max | 33.2 deg | 36.2 mm |
| Mean | 33.2 deg | 36.2 mm |

Applicant found during testing that formulations of the present invention yielded desirable droplet sizes for sublingual administration. The testing also revealed that the formulation dose remains consistent when administered with a spray pump.

We claim:

1. A stable sublingual spray formulation comprising
   from about 20 to about 40% diclofenac, or a salt thereof;
   from about 15 to about 45% water;
   from about 5 to about 35% ethanol;
   from about 5 to about 35% of propylene glycol; and
   from about 1 to about 30% of polyethylene glycol 400.

2. The stable sublingual spray formulation of claim 1 wherein the diclofenac salt is potassium or sodium salt.

3. The stable sublingual spray formulation of claim 1 wherein the polar solvent is selected from the group consisting of water, ethanol, and a combination thereof.

4. The stable sublingual spray formulation of claim 1 wherein the co-solvent is selected from the group consisting of propylene glycol, a low molecular weight polyethylene glycol, and a combination thereof.

5. The stable sublingual spray formulation of claim 1 further comprising an excipient selected from the group consisting of one or more permeation enhancers, flavoring agents, sweeteners, sweetness enhancers, taste-masking agents, and a combination thereof.

6. The stable sublingual spray formulation of claim 5 wherein the one or more flavoring agents is peppermint oil, the one or more sweeteners is sucralose, the one or more sweetness enhancers is ammonium salt of glycyrrhizic acid, and the one or more taste-masking agents are sodium chloride and polyethoxylated castor oil.

7. The stable sublingual spray formulation of claim 1 that is capable of producing a droplet size distribution wherein greater than 98% of the composition particles are greater than 10 microns in diameter during administration.

8. The stable sublingual spray formulation of claim 1 that is capable of producing a droplet size distribution wherein
   a) the mean Dv(10) is from about 10 to about 40 microns during administration;
   b) the mean DV(50) is from about 50 to about 180 microns during administration; and
   c) the mean DV(90) is from about 300 to about 700 microns during administration.

9. The stable sublingual spray formulation of claim 1 that is capable of producing a spray span ((Dv90−Dv10)/Dv50) of from about 1.5 to about 8.

10. The stable sublingual spray formulation of claim 1 that is capable of producing
    a) a spray that has an ovality ratio of from about 1.1 to about 2;
    b) a spray plume width that is from about 10 to about 50 millimeters during administration; and
    c) a spray plume angle that is from about 20 to about 50 degree during administration.

11. A method of treating pain comprising administration of the stable sublingual spray formulation of claim 1 to a patient in need thereof.

12. The method of claim 11 wherein the pain is selected from the group consisting of acute migraine, osteoarthritis, rheumatoid arthritis, and inflammation associated pain.

13. The method of claim 11 wherein from about 50 to about 200 microliters (μL) of the sublingual spray formulation of claim 1 is administered to the patient.

14. A method of treating inflammation comprising administration of the stable sublingual spray formulation of claim 1 to a patient in need thereof.

15. A method of preventing crystal growth in a diclofenac sublingual spray formulation comprising adding at least 5% propylene glycol, at least 1% polyethylene glycol, and less than 50% water.

16. The stable sublingual spray formulation of claim 1 comprising
    from about 20 to about 35% diclofenac, or a salt thereof.

17. The formulation of claim 16 comprising
    from about 20 to about 30% diclofenac, or a salt thereof;
    from about 20 to about 40% water;
    from about 10 to about 30% ethanol;
    from about 5 to about 25% of propylene glycol; and
    from about 1 to about 20% polyethylene glycol 400.

18. The formulation of claim 16 comprising
    from about 25 to about 35% water;
    from about 15 to about 25% ethanol;
    from about 10 to about 20% of propylene glycol; and
    from about 5 to about 15% polyethylene glycol 400.

* * * * *